United States Patent
Riley, III et al.

(10) Patent No.: US 11,344,328 B2
(45) Date of Patent: May 31, 2022

(54) DEVICES, SYSTEMS, AND METHODS FOR EPIDERMAL TISSUE HARVESTING

(71) Applicant: Tara Medical Devices, LLC, Farmers Branch, TX (US)

(72) Inventors: John B. Riley, III, Dallas, TX (US); Max Alan Probasco, Plano, TX (US)

(73) Assignee: Tara Medical Devices, LLC, Farmers Branch, TX (US)

( * ) Notice: Subject to any disclaimer, the term of this patent is extended or adjusted under 35 U.S.C. 154(b) by 482 days.

(21) Appl. No.: 16/576,726

(22) Filed: Sep. 19, 2019

(65) Prior Publication Data

US 2021/0085355 A1    Mar. 25, 2021

(51) Int. Cl.
| | |
|---|---|
| A61B 17/322 | (2006.01) |
| A61B 10/02 | (2006.01) |
| A61B 10/00 | (2006.01) |
| A61B 17/30 | (2006.01) |
| A61B 18/08 | (2006.01) |
| A61B 17/00 | (2006.01) |

(52) U.S. Cl.
CPC .......... *A61B 17/322* (2013.01); *A61B 10/02* (2013.01); *A61B 10/0096* (2013.01); *A61B 18/08* (2013.01); *A61B 2017/00761* (2013.01); *A61B 2017/306* (2013.01); *A61B 2017/3225* (2013.01)

(58) Field of Classification Search
CPC .......... A61B 17/322; A61B 2017/3225; A61B 2017/306; A61B 2017/00761; A61B 18/08; A61B 10/02; A61B 10/0233; A61B 10/0266; A61B 10/0283
See application file for complete search history.

(56) References Cited

U.S. PATENT DOCUMENTS

| | | | |
|---|---|---|---|
| 6,048,337 | A | 4/2000 | Svedman |
| 6,071,247 | A | 6/2000 | Kennedy |
| 6,855,133 | B2 | 2/2005 | Svedman |
| 9,610,093 | B2 | 4/2017 | Sabir et al. |
| 2011/0264115 | A1 | 10/2011 | Asrani et al. |

(Continued)

OTHER PUBLICATIONS

Holm, L. Line, et al., "A Suction Blister Protocol to Study Human T-cell Recall Responses In Vivo", Journal of Visualized Experiments, http://www.jove.com/video/57554, Aug. 11, 2018.

(Continued)

*Primary Examiner* — Kathleen S Holwerda
(74) *Attorney, Agent, or Firm* — Johnston IP Law, PLLC

(57) ABSTRACT

In one instance, a medical device for harvesting epidermal tissue from a patient includes a first compartment that is mateable with a second, disposable compartment that goes against the skin. The first compartment has a floor that is formed, at least in part, by a first printed circuit board. The ceiling of the second, disposable compartment is formed at least in part by a second printed circuit board that electrically couples with the first printed circuit board when in a mated position. Suction is delivered to the second compartment to pull skin through apertures on the floor of the second compartment to form blisters that are harvested to obtain epidermal tissue. The first compartment remains uncontaminated in use and the second compartment is disposable. Other features are presented; some of which include a thermal sensor in the second compartment for temperature control, clear side walls, and a distributed heating element.

22 Claims, 13 Drawing Sheets

(56) References Cited

U.S. PATENT DOCUMENTS

| | | |
|---|---|---|
| 2012/0172894 A1 | 7/2012 | Sabir et al. |
| 2013/0204273 A1 | 8/2013 | Sabir et al. |
| 2015/0182242 A1* | 7/2015 | Pratt .................... A61B 17/322 606/132 |
| 2020/0163688 A1* | 5/2020 | Kieswetter ........... A61B 5/0531 |

OTHER PUBLICATIONS

Electronic Diversities, "Negative Pressure Instrument", http://www.electdiv.com/page4.html, Rev 2008.
KCI, "Epidermal Harvesting", https://mykci.com/products/cellutome-epidermal-harvesting-system, printed on Sep. 19, 2019.

* cited by examiner

DEVICES, SYSTEMS, AND METHODS FOR EPIDERMAL TISSUE HARVESTING

TECHNICAL FIELD

This application is directed, in general, to medical devices, and more specifically, to devices, systems, and methods for harvesting epidermal tissue from a patient.

BACKGROUND

Human skin is one of the most important organs and is the largest. Skin is responsible for protection, regulation, and sensation. Dermatology is devoted to treating and caring for the skin of humans.

Dermatologists have developed many techniques for treating skin conditions. One technique for addressing chronic wounds and other conditions is a kind of skin graft technique known as suction blistering. With this technique, epidermal tissue is harvested through the formation of suction blisters typically without anesthesia that are cut or otherwise removed for transportation to another site.

Suction blistering may also be used for research or other purposes. In addition, suction blistering may be used with animals for various reasons, including research.

SUMMARY

According to one illustrative embodiment, a medical device for harvesting epidermal tissue from a patient includes a first compartment that is releasably coupled to a second compartment. The first compartment includes a first floor member comprising a first printed circuit board and having a first side and a second side, wherein the second side is outward facing; a first plurality of side walls coupled to the first floor member; and a first ceiling member coupled to the plurality of side walls. The first floor member, the first plurality of side walls, and the first ceiling member form the first compartment having a first interior portion and a first exterior shell. The medical device further includes a plurality of conductive wires coupled to the first printed circuit board.

The second compartment includes a second floor member having a first side and a second side, wherein the second side is outward facing, and wherein the second floor member is formed with one or more apertures for receiving a portion of the patient's skin; a second plurality of side walls coupled to the second floor member; and a second ceiling member coupled to the plurality of side walls. The second ceiling member has a first side and a second side, wherein the first side of the second ceiling member is outward facing when in an unmated position. The second ceiling member comprises a second printed circuit board that is electrically coupled with the first printed circuit board when in a mated position. The second floor member, the second plurality of side walls, and the second ceiling member form the second compartment having a second interior portion and a second exterior shell, wherein the second compartment forms a substantially fluid-tight compartment except for the one or more apertures for receiving the patient's skin and, of course, the reduced-pressure port that introduces reduced pressure. The medical device further includes a reduced-pressure conduit fluidly coupled to the second interior portion. In the mated position, the first compartment is releasably coupled to the second compartment with the second side of the first floor member facing the first side of the second ceiling member.

According to another illustrative embodiment, a system for harvesting epidermal tissue from a patient includes a control unit. The control unit includes a housing, a reduced-pressure pump within the housing, and an electrical controller. The system further includes a harvesting medical device generally of the type described above.

According to still another illustrative embodiment, a method of harvesting epidermal tissue from a patient includes providing a medical device of the generally described above and applying reduced pressure to the interior of the second compartment to pull the patient's skin into the one or more apertures through the second floor member. The method further includes applying electrical power to the heating element on the second printed circuit board and removing epidermal tissue once one or more blisters are formed that extend through the one or more apertures through the second floor member.

According to one illustrative embodiment, a medical device for harvesting epidermal tissue from a patient includes a first compartment that is mateable with a second, disposable compartment that contacts the skin. The first compartment has a floor that is formed, at least in part, by a first printed circuit board. The ceiling of the second, disposable compartment is formed at least in part by a second printed circuit board that electrically couples with the first printed circuit board when in a mated position. Suction is delivered to the second compartment to pull skin through apertures on the floor of the second compartment to form blisters that are harvested to obtain epidermal tissue. The first compartment remains uncontaminated in use and the second compartment is disposable. Other embodiments and features are disclosed herein.

DESCRIPTION OF THE DRAWINGS

Illustrative embodiments of the present invention are described in detail below with reference to the attached drawing figures, which are incorporated by reference herein and wherein.

DETAILED DESCRIPTION

In the following detailed description of the preferred embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the claims.

Unless otherwise indicated, as used throughout this document, "or" does not require mutual exclusivity.

Figure 1:
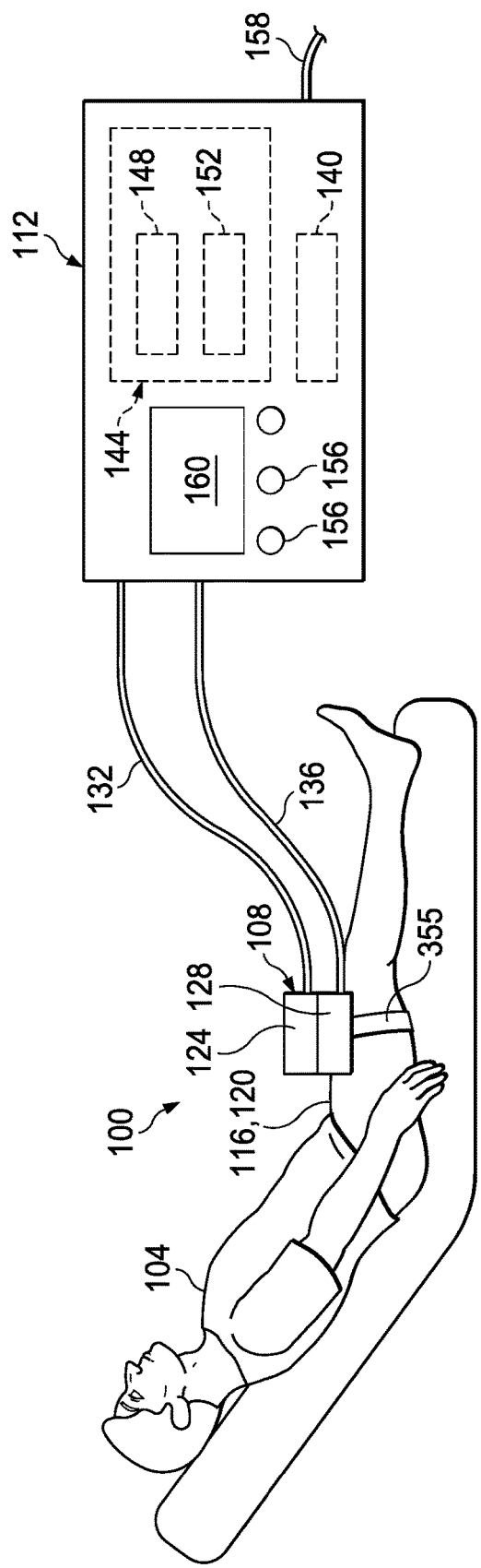
FIG. 1 is a schematic representation of the patient undergoing an epidermal tissue harvesting procedure using an illustrative embodiment of an epidermal tissue harvesting system.

Referring now to the figures, and initially to FIG. 1, a system 100 for harvesting epidermal tissue from a patient 104 is presented. While a human patient is shown, it should be understood that the devices, systems, and methods herein may also be used on animals, and the term "patient" is meant to include the same. The epidermal tissue may be harvested for any of a number of uses including wound care, medical research, animal research, cell harvesting (e.g., melanocyte harvesting), or other purposes. The system uses suction, or reduced pressure, with heat, to form blisters that separate the epidermis from the dermis so that the epidermis can be harvested for epidermal skin grafting or for the purposes previously mentioned or other uses.

As used herein, "reduced pressure" generally refers to a pressure less than the ambient pressure at a tissue site that is being subjected to harvesting. In most cases, this reduced pressure will be less than the atmospheric pressure at which the patient is located. Alternatively, the reduced pressure may be less than a hydrostatic pressure at the tissue site. Unless otherwise indicated, quantitative values of pressure stated herein are gauge pressures. The reduced pressure delivered may be constant or varied.

The system 100 includes a medical device, or harvesting medical device 108 and a control unit 112, or control console. The medical device 108 contacts a portion of the patient's 104 skin 116, such as on a leg 120 or arm or other location. The medical device 108 has a first compartment 124, or head housing, and a second compartment 128, or disposable chamber. A conductor cable, or electrical cable 132, electrically couples electronic components within the first compartment 124 to the control unit 112. A reduced-pressure conduit 136, or suction line, fluidly couples the second compartment to a fluid pump 140, e.g., an air pump, in the control unit or elsewhere. The reduced pressure is used to pull skin into apertures to form blisters as will be explained further below. While pressure ranges may vary in different embodiments, in one embodiment, the pressure is adjustable down to full vacuum (−760 mm Hg/−30 inches Hg) and may be set at any pressure between atmospheric and full vacuum. In one illustrative embodiment, the procedure range is between −300 mm Hg and −500 mm Hg.

The control unit 112 includes an electrical controller 144 that has at least one processor 148 and at least one memory unit 152 associated with the processor 148. The memory unit 152 may comprise one or more of the following: volatile media, nonvolatile media, removable media, non-removable media, computer storage media, and may include instructions implemented in a method or technology for storage of information, such as computer readable instructions, data structures, program modules, or other data. The processor 148 may comprise one or more microcontrollers, or other circuitry typically found in a microprocessor, such as an execution unit, bus interface unit, Arithmetic Logic Unit ("ALU"), and the like. In some cases, the processor and memory unit(s) may be embodied in a single Integrated Circuit ("IC") chip.

The control unit 112 with its processor 148 and memory 152 may carry out instructions to manage the medical device 108, such as a feedback loop for temperature whereby input for temperatures are received and the amount of power supplied to the heating element is adjusted in response thereto. The control unit 112 may allow a specific temperature or range to be entered using input controls 156 and may display current parameters (e.g., actual temperature, target temperature, elapse time of treatment) on an output device, e.g., screen 160. The control unit 112 may optionally display text and graphics, may include an audible alarm, a vacuum/reduced-pressure gauge, adjustable vacuum regulator, and other components. The control unit 112 may include electronics for a communications interface, e.g., universal serial bus (USB), that may be used to connect to a personal computer, data logging device, or other device. The control unit 112 may include power cord 158 for energizing the control unit 112. The power cord 158 may be used to receive power for the system 100 of various parameters: 110-120 VA 60 Hz for North America or 220-24 VAC 50/60 Hz for Europe, Asia, Africa, or elsewhere.

In this illustrative embodiment, the second compartment 128 forms a fluid-tight compartment, except one or more apertures on a floor into which skin is drawn and the reduced-pressure port that supplies the reduced-pressure/vacuum. The second compartment 128 is the only portion of the medical device 108 that comes into contact with the patient and that is subjected to contamination. A printed circuit board (PCB) forms a portion of a ceiling of the second compartment that provides the fluid-tight interior compartment. The PCB forms or helps form a barrier to contain any body fluids that might otherwise leak during a procedure. The first compartment 124 mates with the second compartment 128 and is electrically coupled to the second compartment 128 but sealed from contamination by body fluids. The second compartment 128 is disposable; namely, the second compartment 128 is intended for only one use and then is thrown away. At a functional level, this may mean that the second compartment 128 has fully-loaded cost that is below the expense of cleaning and repackaging the second compartment 128. In some embodiments, the second compartment 128 is not disposable, but may be appropriately cleaned and reused.

As used herein, the term "coupled" in a mechanical context includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. "Fluid coupling" means that fluid may be in communication between the designated parts or locations. "Electrical coupling" means the two designated parts or location may have electrical flow between them. As used herein, "fluid" is a substance (such as a liquid or gas) tending to flow or conform to the outline of its container; a fluid may be a gas or a liquid.

Figure 2:
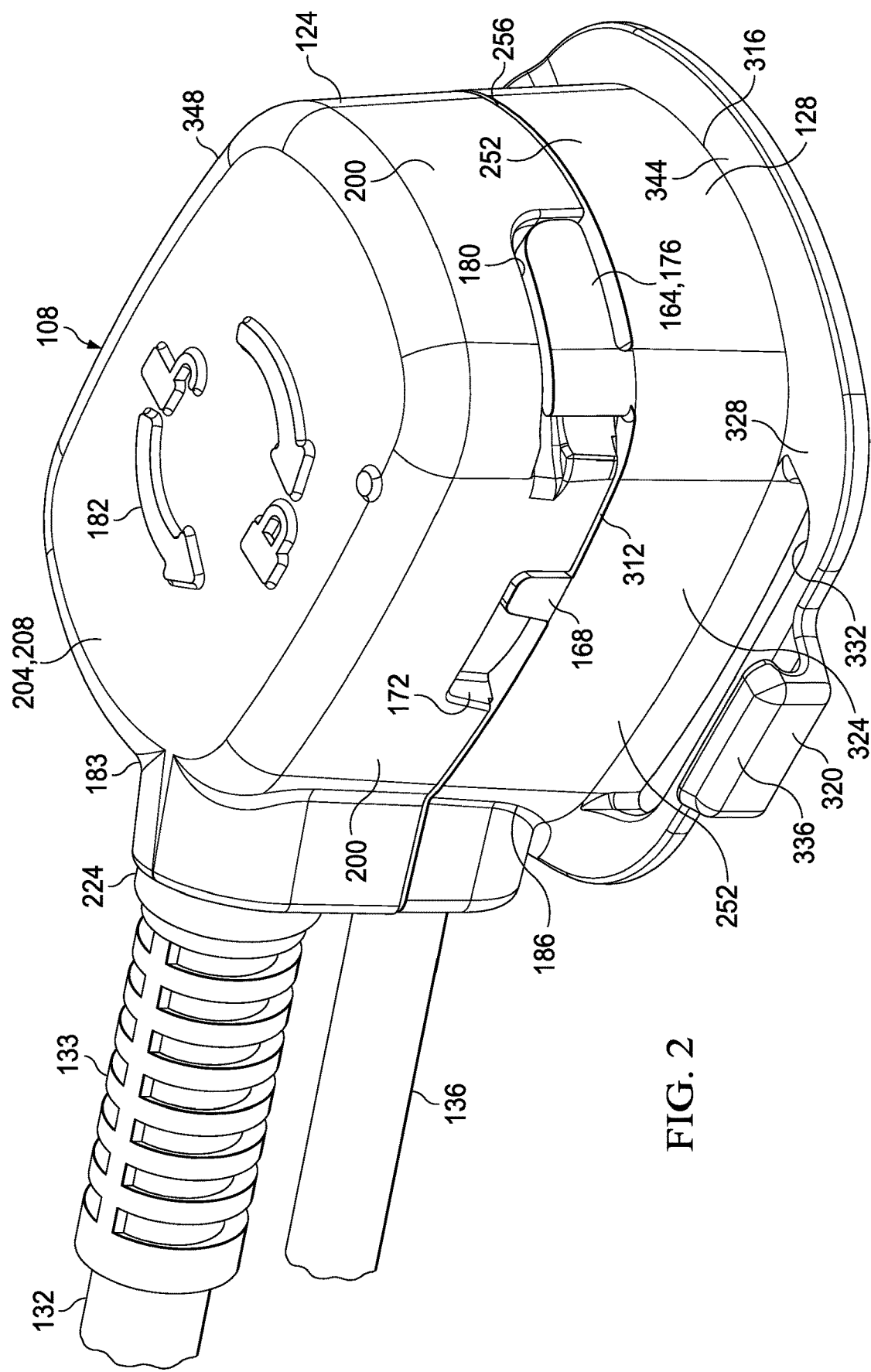
FIG. 2 is a schematic, perspective view of an illustrative embodiment of a medical device for harvesting epidermal tissue from a patient shown in a mated, or assembled, position.
Figure 3:
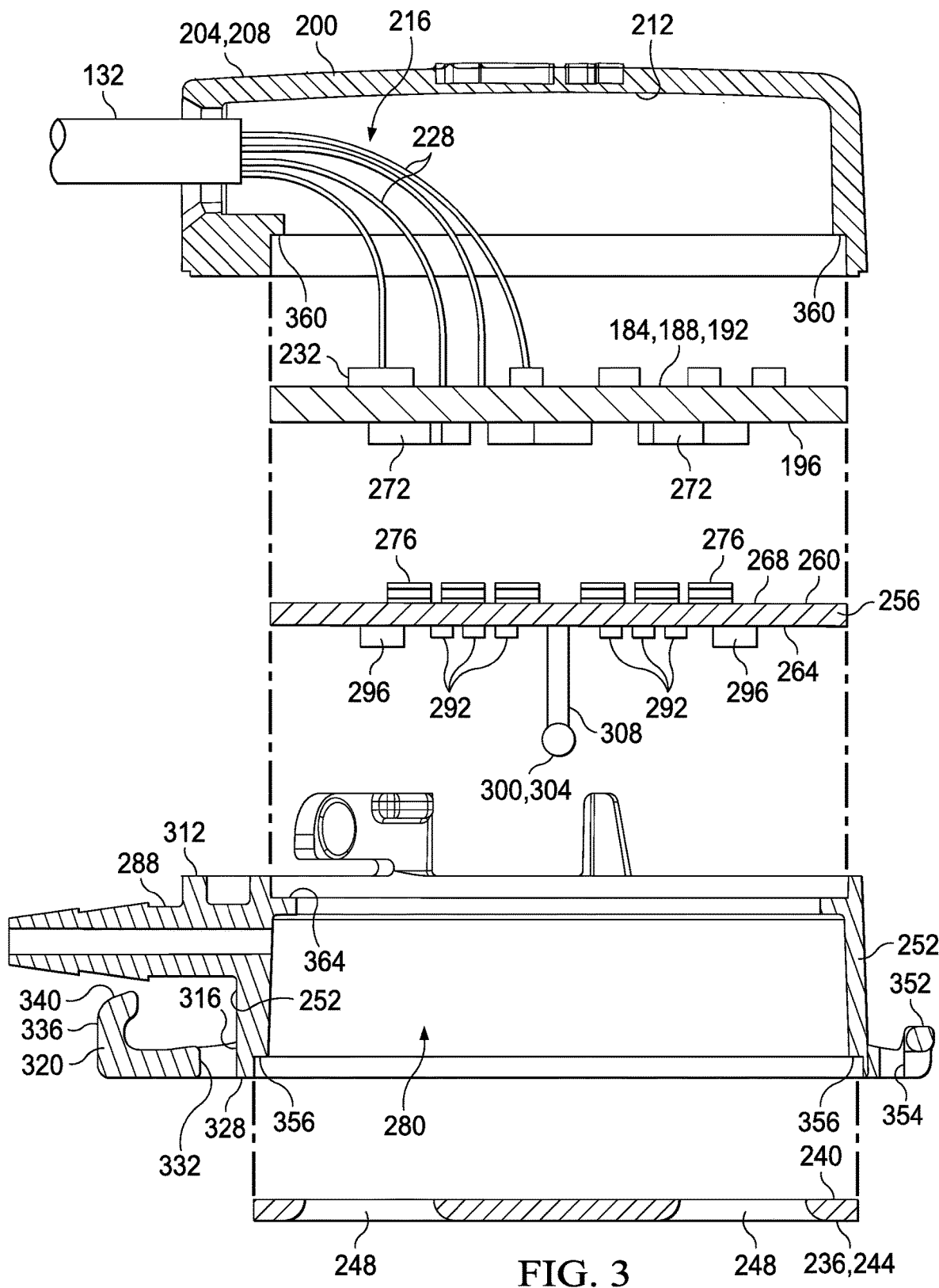
FIG. 3 is a schematic, exploded, side cross section of an illustrative embodiment of a medical device for harvesting epidermal tissue from a patient.

Referring now primarily to FIG. 2 and also to FIG. 3, a schematic, perspective view of an illustrative embodiment of a medical device 108 for harvesting epidermal tissue from a patient 104 is shown in a mated, or assembled, position. The mated position is when the first compartment 124 and the second compartment 128 have been releasably coupled, such as by a twist lock 164.

The twist lock 164 may include a first guide pin 168 that is fitted to remain in a first pin-socket 172. There is a similar pin and socket on the other side as shown FIGS. 3 and 6. The twist lock 164 also includes a first latch member 176 that interfaces with a latching socket 180. As indicated by visual indicia 182, rotating clockwise with the pins in the sockets and the latching member in the latching socket will releaseable couple the first compartment 124 to the second compartment 128. To unlock, again as suggested by visual indicia 182, the first compartment 124 and second compartment 128 are rotated counter clockwise.

Those skilled in the art will appreciate that any of a number of releasable securing devices or techniques may be used to releasably couple the first compartment 124 to the second compartment 128. For example, the coupling may be accomplished with an interference fit of members, clasp between them, clipping member, push-pull interface, snaplock, a strap, a latch, hook-and-loop, twist lock, clamp, screw, lock, snap, hitch, pin, cam, spring clip, snap fastener, rivet or other fastener.

In this view, one can see the conductor cable 132 entering on a corner 183 of the first compartment 124. The conductor cable 132 may have a strain relief member 133, e.g., a rubber strain relief cord boot protector, over a portion of the conductor cable 132 proximate the first compartment 124. Likewise, the reduced-pressure conduit 136 is shown entering on a corner 186 of the second compartment. The corners 183, 186 are convenient for cable/conduit management, but those skilled in the art will appreciate that other locations might be used.

Figure 12:
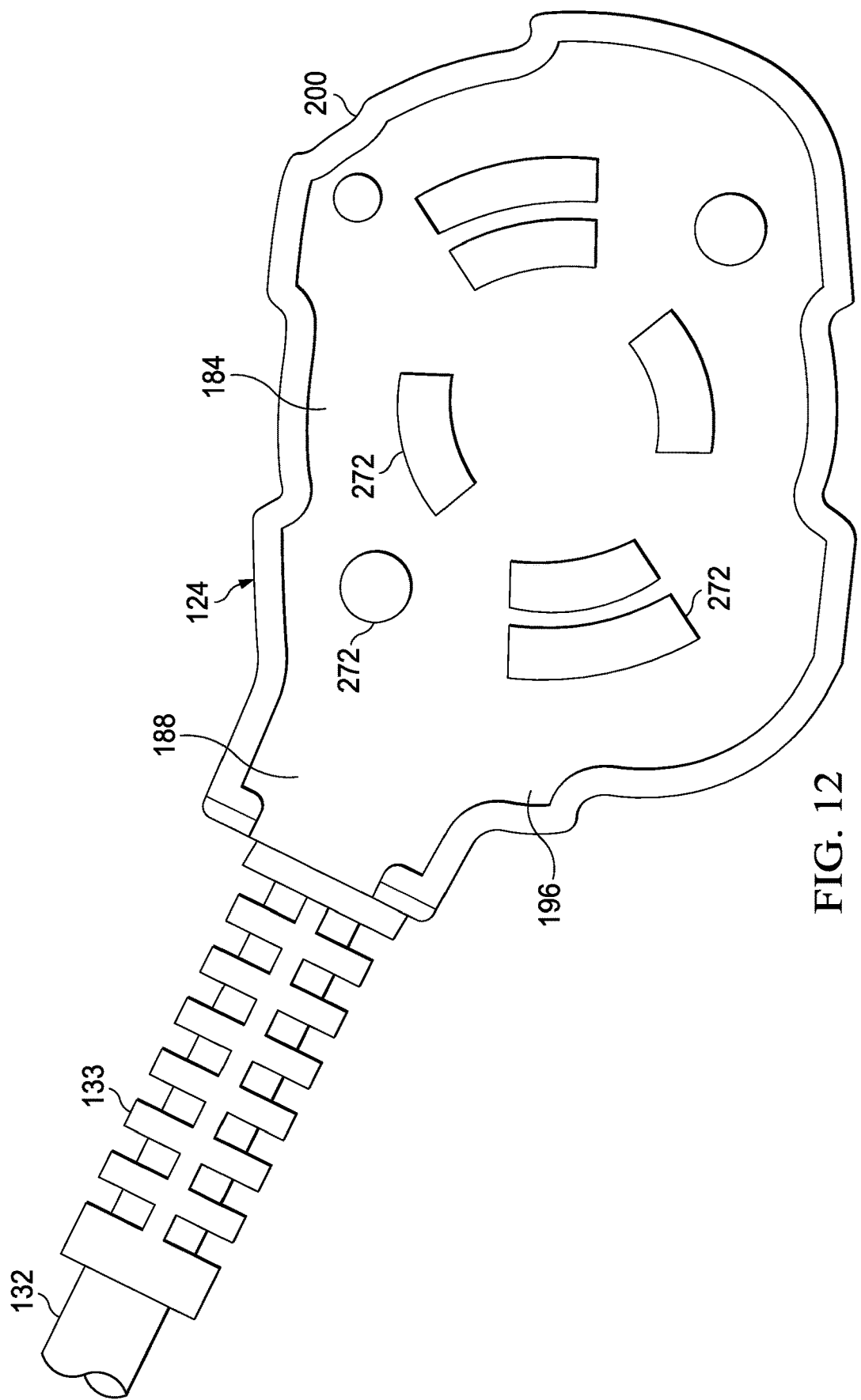
FIG. 12 is a schematic, bottom plan view of a first compartment of an illustrative embodiment of a medical device for harvesting epidermal tissue from a patient.

Referring momentarily to FIG. 12, which shows a bottom view of the first compartment 124, the first compartment 124 is formed with a first floor member 184 comprising a first printed circuit board 188 and having a first side 192 (FIG. 3) and a second side 196. The first printed circuit board 188 may form all or a portion of the first floor member 184. The second side 196 of the first floor member 184 is outward facing in an unmated position. Referring again primarily to FIG. 2, the first compartment 124 further includes a first plurality of side walls 200 coupled to the first floor member 184 and a first ceiling member 204 coupled to the plurality of side walls 200. The ceiling member 204 has a first side 208, which is outward facing. The first side 208 is a top side for the orientation shown. It should be understood that the terms "top," "side," and "bottom" and like terms are for the orientations shown and are not mean to be absolute orientations or limiting. The ceiling member 204 has a second side 212 (FIG. 3) that is opposite the first side 208.

The first floor member 184, the first plurality of side walls 200, and the first ceiling member 204 form the first compartment 124 having a first interior portion 216 (FIG. 3) and a first exterior shell 220, or surface. The first exterior shell 220 may be formed with a conductor-cable aperture 224 (see also, FIG. 11) for receiving the conductor cable 132. The conductor cable 132 electrically couples the first printed circuit board 188 (FIG. 3) and the electrical controller 144 (FIG. 1) in the control unit 112 (FIG. 1). The conductor-cable aperture 224 is shown formed on or proximate the corner 183 but could be located at other positions. The conductor cable 132 may include a plurality of conductive wires 228 (FIG. 3) coupled to the first printed circuit board 188 such as on first contacts/pads 232 (FIG. 3) or through an electrical connector. As used herein, "contact/pad" is meant in a broad sense and include an electrical connection point. Those skilled in the art will understand that the first printed circuit board 188 and the second printed circuit board 256 may include other electronic components, including, without limitation, drivers, analog to digital converters, filters, amplifiers, discrete components, etc.

The second compartment 128 includes a second floor member 236 (FIG. 3), or orifice plate, having a first side 240 and a second side 244. The second side 244 is outward facing and is what is placed against the patient's skin. The second floor member 236 is formed with one or more apertures 248 for receiving a portion of the patient's skin (see FIG. 13). As shown elsewhere, the one or more apertures 248 are formed with rounded corners or edges on the aperture opening where the skin is pulled inward, i.e., the outermost edge of the apertures; this is for patient comfort. For this reason, the one or more apertures 248 may be referred to as a rounded aperture or a plurality of rounded apertures. Each of the apertures 248 has at least a rounded corner at the entrance from the second side of the second floor member. In some embodiments, the second floor member 236 may have an increased thickness to allow a larger radius of the edge, or rounded edge. In some embodiments, the edge of the at least one aperture may not be rounded but may be orthogonal.

One illustrative embodiment uses a 1.6 mm thick plastic (polycarbonate) orifice plate, or second floor member 236. In another illustrative embodiment, the second floor member 236 is formed from aluminum with a thickness of 30 mils (0.76 mm). Other thicknesses and materials may be used.

The second compartment 128 also includes a second plurality of side walls 252 coupled to the second floor member 236. The second plurality of side walls 252 may be formed from a transparent plastic to allow a clinician to view the formation of blisters and to be able to visually detect when the blisters are ready for harvesting.

The second compartment 128 further includes a second ceiling member 256 (FIG. 3) coupled to the plurality of side walls 252. The second ceiling member 256 has a first side 260 (FIG. 3) and a second side 264 (FIG. 3). The first side 260 is the top side for the orientation shown. The first side 260 of the second ceiling member 256 is outward facing when in an unmated position. The second ceiling member 256 is formed at least in part by a second printed circuit board (PCB) 268. In some embodiments, the second printed circuit board 268 forms the entire second ceiling member 256 and in others only a window or a portion of it. The second printed circuit board 268 is electrically coupled with the first printed circuit board 188 when in a mated position. For example, electrical contacts/pads 272 on the second side 196 of the first circuit board 188 electrically couple with complimentary electrical contacts/pads, 276.

In some embodiments, the second side 264 of the second ceiling member 256 on the second printed circuit board 268 includes a heating element, e.g. a heating trace 292 (FIG. 3) or flexible resistive heater (e.g. polyimide substrate with copper traces), that may extend over a majority of the surface of the second side 264 of the second ceiling member 256 on the second printed circuit board 268. Some embodiments may include a flexible resistive heater (e.g. polyimide substrate with copper traces) mounted to the second side 264 of the second ceiling member board 256 as the heating element and as part of the second PCB 268. The heating element 292 as shown allows heat to be introduced directly in the second compartment 128 in the second interior portion 280. In another alternative embodiment, the heating element is positioned on the first side 260 of the second ceiling member 256. One or more LED lights 296 may also be coupled to the second side 264 of the second ceiling member 256 to illume the skin or blisters. The LED lights 296 are typically on the second printed circuit board 268 itself and electrically coupled to a power lead thereon. Again, other electronics or sensors, e.g., IR element, may be added to the second ceiling member 256.

A thermal sensor 300 (FIG. 3), e.g. a thermistor 304, a infrared unit, or a thermocouple, may also be coupled to the second side 264 of the second ceiling member 256 and typically to the second printed circuit board 268. The thermal sensor 300 may have an extension conduit 308, or extension member, to suspend the thermal sensor 300 in the middle of the second interior portion 280. In an embodiment in which the thermal sensor 300 is an infrared unit, the extension conduit 308 is typically excluded. In this way, the temperature in the second compartment 128 is measured directly for accuracy and need not be estimated (which is required when the thermal sensor is not located directly in the second chamber 128) or determined using an algorithm or estimating technique. The temperature data from the thermal sensor 300 may be communicated by the conductor cable 132 to the control unit 112 (FIG. 1) in digital or analog form to allow for a feedback control. Based on the temperature information from the thermal sensor 300, the power supplied to the heating element 292 may be adjusted.

The second floor member 236, the second plurality of side walls 252, and the second ceiling member 256 form the second compartment 128. The second compartment 128 has a second interior portion 280 (FIG. 3) and a second exterior shell 284, or surface. The second compartment 128 forms a substantially fluid-tight compartment except for the one or more apertures 248 for receiving the patient's skin and the reduced-pressure port 288 (FIG. 3).

The second compartment 128 is formed with a reduced-pressure port 288 through the second exterior shell 284 for coupling with the reduced-pressure conduit 136 that fluidly couples the second interior portion 280 to the reduced-pressure pump, or fluid pump 140 (FIG. 1) of the control unit 112.

As shown clearly in FIG. 2, in the mated position, the first compartment 124 is releasably coupled to the second compartment 128. In that position, the second side 196 of the first floor member 184 (FIG. 12) faces the first side 260 of the second ceiling member 256. Moreover, in the embodiment shown in FIGS. 9 and 12, the contacts/pads 272 and 276 touch to form an electrical coupling as well.

The second plurality of side walls 252 has a first portion 312 proximate the second ceiling member 256 and a second portion 316 proximate the second floor member 236. A first securing arm 320 extends from a first side 324 of the second plurality of side walls 252 proximate the second portion 316 of the second plurality of side walls 252. The first securing arm 320 includes an extension portion 328, which extends substantially perpendicular to the second side walls 252, formed with a first strap aperture 332. The first securing arm 320 includes a gripping portion 336 with a hook-shaped end 340. The extension portion 328 may be part of an apron 344 that extends around the second plurality of side walls 252. On the other side, or second side 348 of the side walls 252, a second securing arm 352 (FIG. 3) extends from the second side of the second plurality of side walls 252 proximate the second portion 316 of the second plurality of side walls 252. The second securing arm 252 is analogous to the first securing arm 320 with an extension portion and a second strap aperture except it does not have a gripping portion or hook-shaped end.

Figure 14:
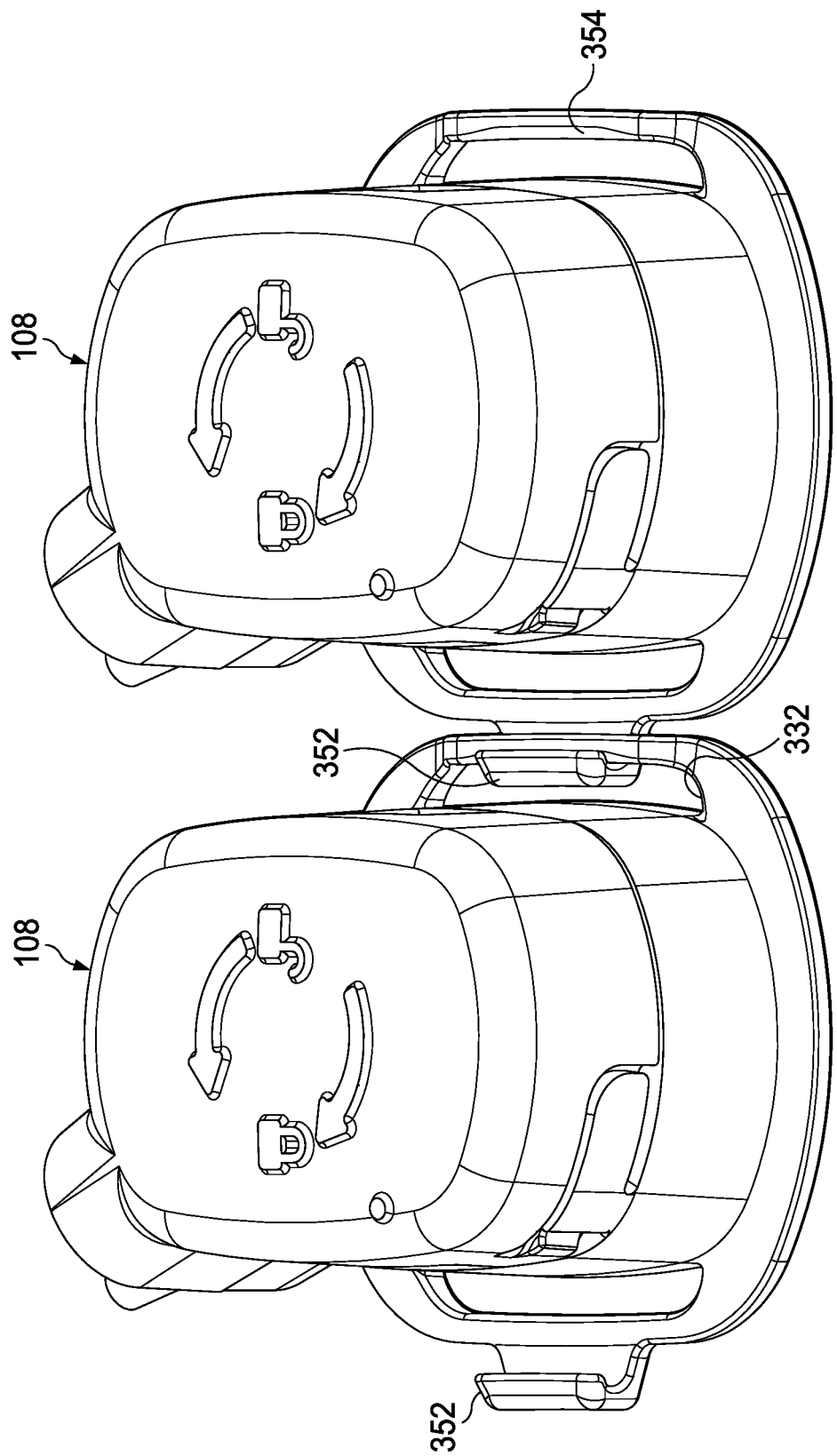
FIG. 14 is a schematic, perspective view showing illustrative embodiments of two medical devices for harvesting epidermal tissue from a patient coupled together.

The securing arms 320, 352 allow the medical device 108 to be releasably coupled to the patient. A securing strap 355 (FIG. 1) can be looped through the strap aperture 332 of one arm and to the strap aperture on the other securing arm 354 to secure the second floor member 236 against the patient's skin during treatment. The first securing arm 320 may also be used to couple two medical devices 108 to each other as shown in FIG. 14. In such a case, the two harvesting medical devices 108 may be placed adjacent to each other with the securing arm 320 and in particular the gripping portion 336 of one device into the strap aperture 332 of the securing arm of the adjacent device. When the strap is applied to the strap apertures of the two outside securing arms, the two medical devices will be held adjacent and securely in place at their interface by the gripping portion 336 and the aperture 332. In this way, the harvesting area can be readily doubled. A third device 108 or even more devices could be daisy chained in this fashion.

An interior portion of the plurality of side walls 252 may be formed proximate the second portion 316 with a ledge 356 for receiving the second floor member 236. This facilitates coupling and sealing. In a similar fashion, a bottom portion (for orientation shown) of the first plurality of side walls 200 may be formed with a ledge 360 for receiving the first floor member 184.

In some embodiments, the first plurality of side walls 200 and the first ceiling member 204 are formed as an integral unit by injection molding of plastics, additive manufacturing (3D printing), or subtractive manufacturing (e.g., machining). The first floor member 184, which may just be the first printed circuit board 188, may be then be coupled using the ledge 360 and held in place with screws, adhesive, sealant or other fastening technique. Similarly, the second plurality of sidewalls 252 may be formed by injection molding or the other techniques mentioned. The second floor member 236 may then be coupled onto ledge 356 at the second portion and the second ceiling member 256 coupled at the first portion using ledge 364. Glues or epoxies may be used as well or interference fits. The second compartment 128 is fluid-tight except for the apertures 248 and reduced-pressure port 288.

Referring again primarily to FIG. 3, a schematic, exploded, side cross section of an illustrative embodiment of the medical device 108 for harvesting epidermal tissue from a patient 104 is presented. The first compartment 124 is intended to be reusable and the second compartment 128 is intended to disposable (although in other embodiments, the second compartment 128 may be cleaned and reused). In embodiments in which the second compartment 108 is disposable, there is no cleaning required; it is simply thrown away after use. The disposable nature of the second compartment 128 eliminates cross-patient contamination risk. The second compartment 128 is fluid-tight other than the apertures 148 and the reduced-pressure port. The second ceiling member 256 is in this embodiment formed completely by the second printed circuit board 268, which includes LED lights 296, heating element 292, and thermal sensor 300. Other electronic components may be mounted to the second circuit board 268 as desired.

Figure 4:
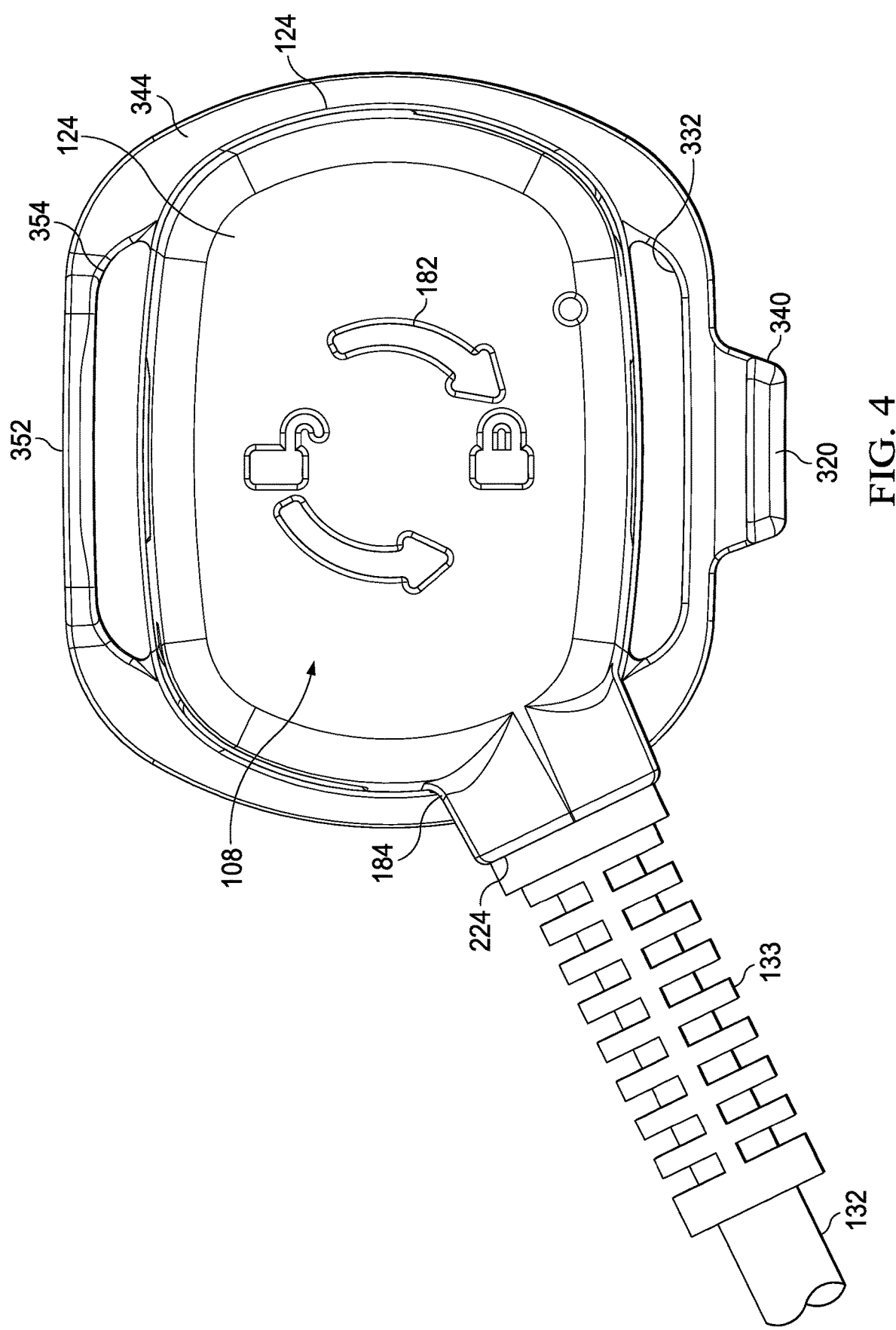
FIG. 4 is a schematic, top plan view of the device of FIG. 2.

Referring now primarily to FIG. 4, a schematic, top plan view of the medical device 108 is presented. In this view it will be appreciated, that as indicated by the visual indicia 182, twisting the first compartment 124 relative to the second compartment 128 will allow them to separate when turned counterclockwise and to lock when turned clockwise. This view also clearly shows the conductor cable or sheath 132 entering the conductor-cable aperture 224 at corner 183. Other attachment arrangements are contemplated between the first compartment 124 and the second compartment 128 as noted elsewhere herein.

Figure 5:
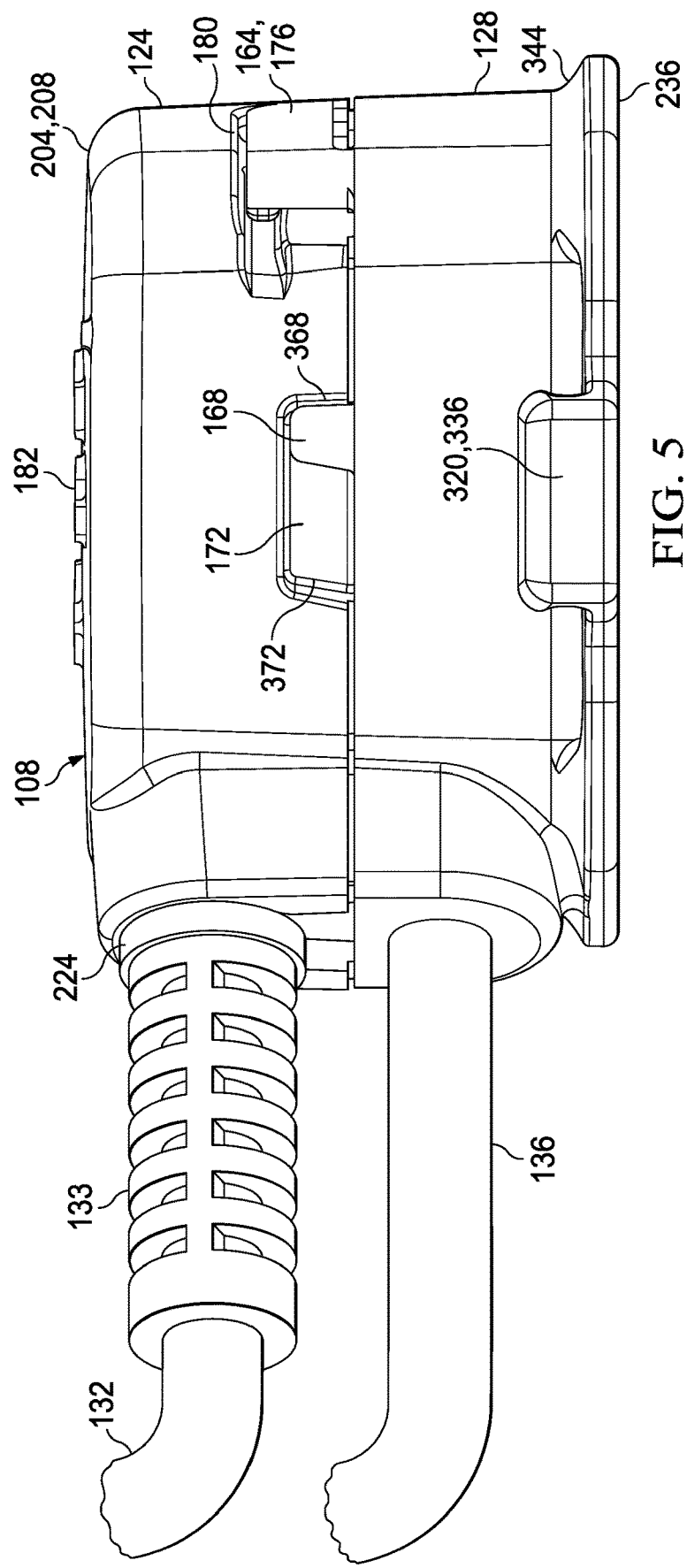
FIG. 5 is a schematic, perspective view from a side of the device of FIG. 2.

Referring now primarily to FIG. 5, a schematic, perspective view from a side of the medical device 108 is presented. This view clearly shows the guide pin 168 in the first pin socket 172. The guide pin 168 is shown to one side 368 of the first pin socket 172 where it resides when in the mated position and is locked. When fully unlocked, the guide pin 168 is at the other end 372 of the first pin socket 172.

Figure 6:
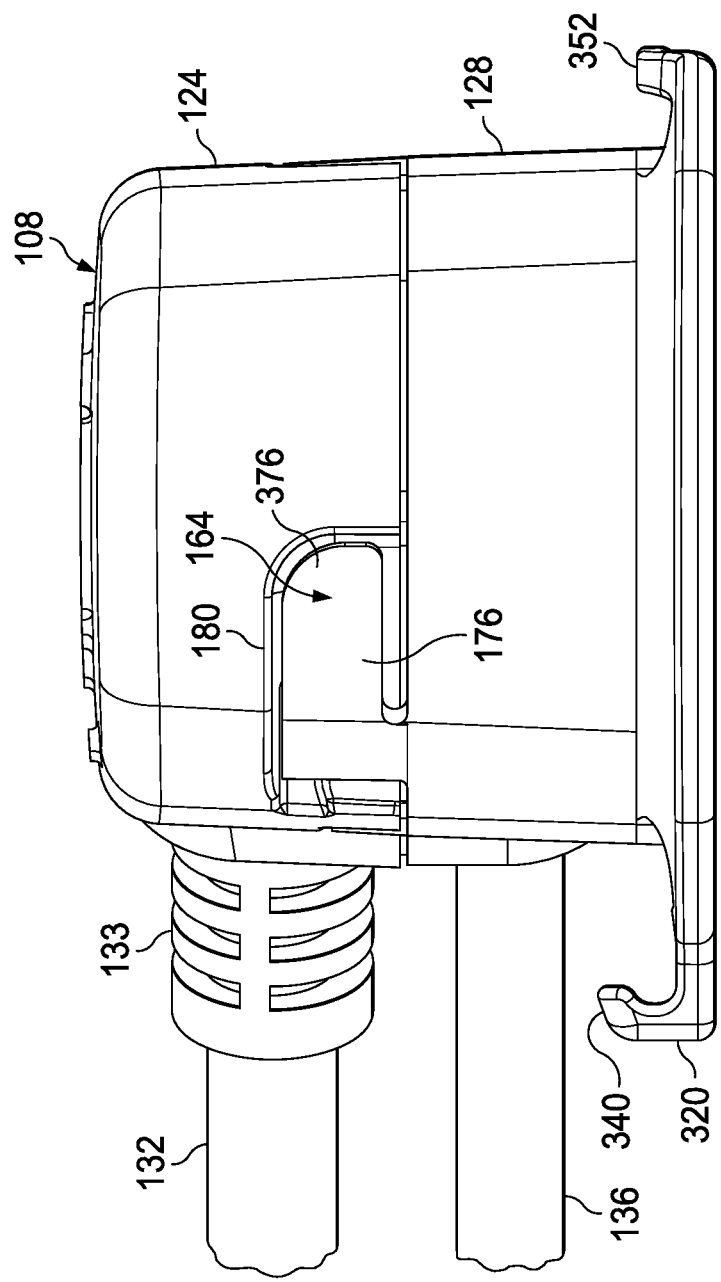
FIG. 6 is a schematic perspective view from one end of the device of FIG. 2.

Referring now primarily to FIG. 6 is a schematic perspective view from one end of the medical device 108 that is slightly rotated from the view of FIG. 5. This view shows the first latch member 176 in a locked position within the latching socket 180. An end portion 376 of the first latch member 176 may have a pin or ball portion urged inward that engages an indention 380 (FIG. 7) on an interior side of the latching socket 180 to hold the first latch member 176 and the latch socket 180 in relative position while locked. When rotated, the pin or ball slides out and allows continued rotation. Those skilled in the art will appreciate that other approaches may be used for a twist lock or other releasable coupling.

Figure 7:
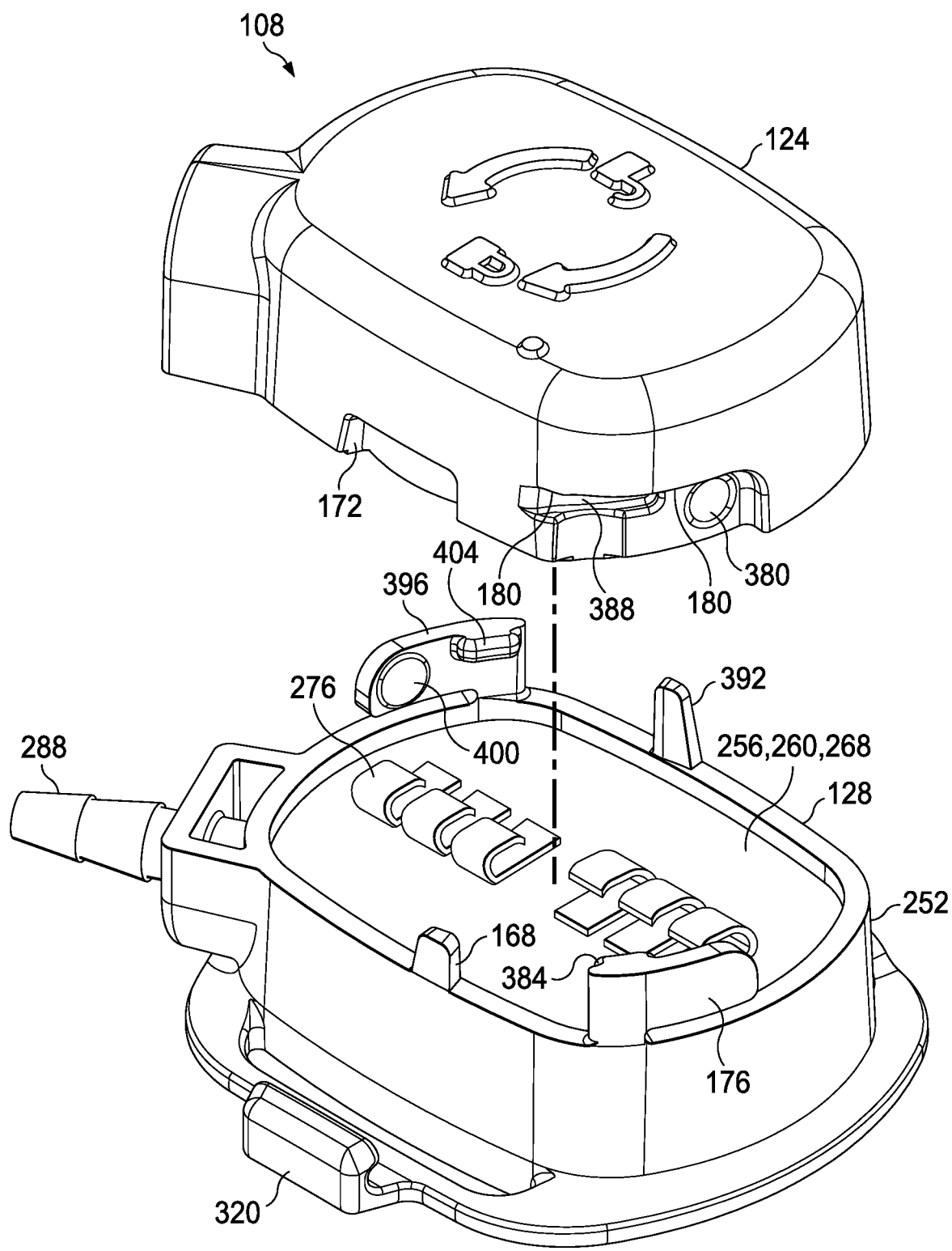
FIG. 7 is a schematic, exploded, perspective view of the device of FIG. 2 showing how the first compartment mates with the second compartment.

Referring now primarily to FIG. 7 is a schematic, exploded, perspective view of the medical device 108 showing how the first compartment 124 mates with the second compartment 128 is presented. In this view, one illustrative embodiment of electrical contacts/pads 276 can be seen on the first side 260 of the second ceiling member 256, which is the second printed circuit board 268, of the second compartment 128. The electrical contacts/pads 276 mate with electrical contacts/pads 272 (FIGS. 3 and 12) of the second side 196 of the first printed circuit board 188 of the first floor member 184 of the first compartment 124. The latch member 180 may include an inward ledge or protrusion 384 that engages a slot 388 formed on the exterior of the first plurality of side walls and in this embodiment in the latching socket 180. The inward ledge 384 further facilitates the twisting lock 164.

Figure 10:
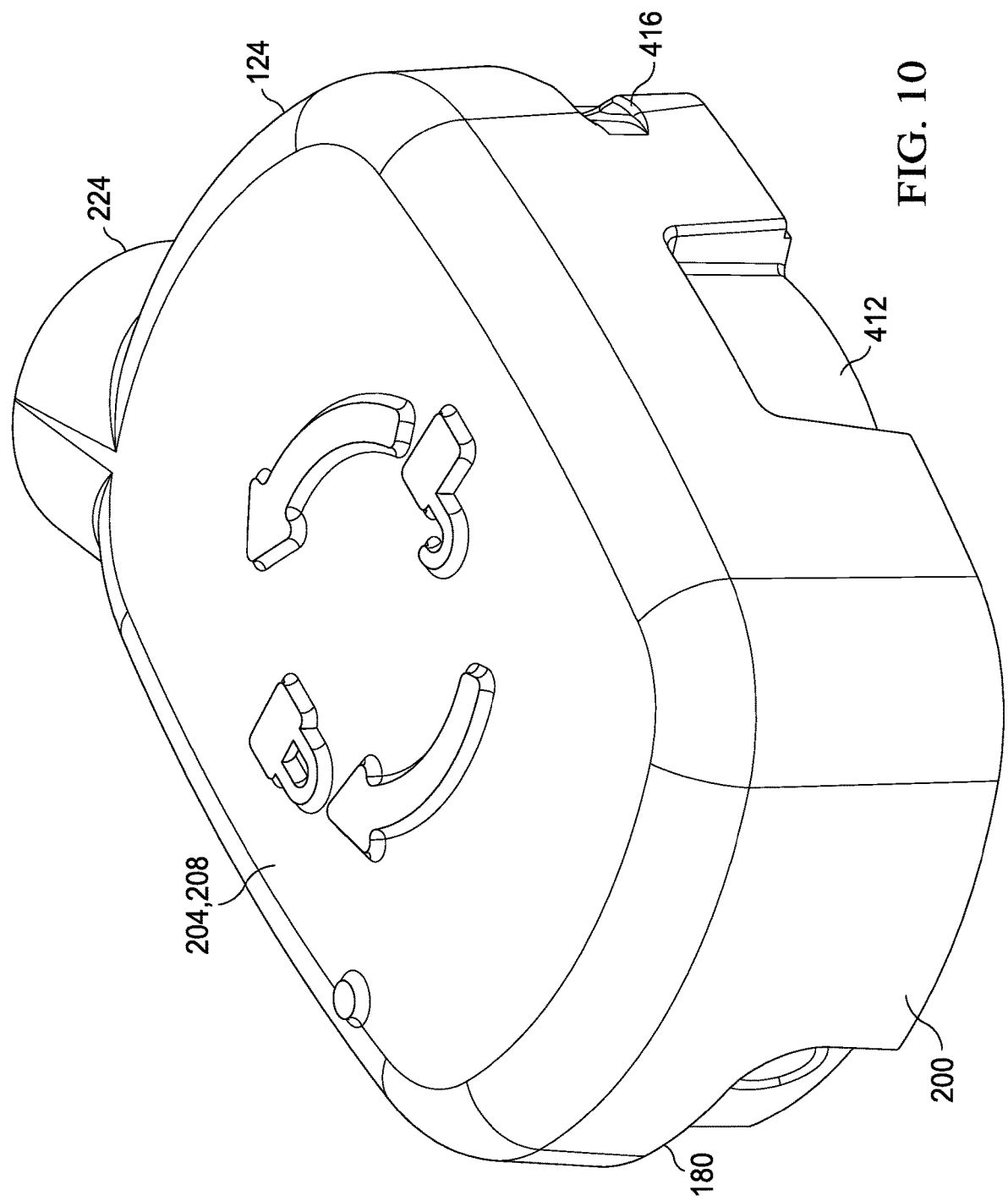
FIG. 10 is a schematic, perspective view from a side of a first compartment of an illustrative embodiment of a medical device for harvesting epidermal tissue from a patient.
Figure 11:
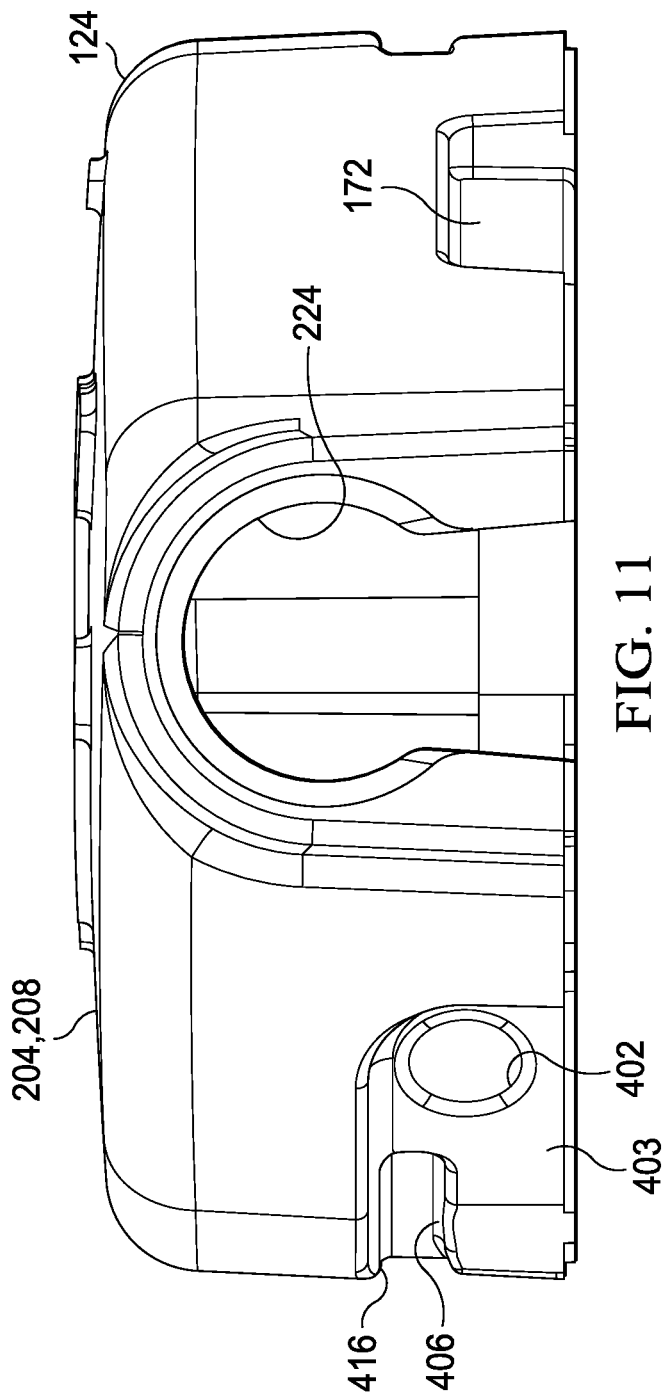
FIG. 11 is a schematic, elevation view of a first compartment of an illustrative embodiment of a medical device for harvesting epidermal tissue from a patient.

This figure also shows a second guide pin 392 that is analogous to the first guide pin 168 and mates with a second guide pin socket 412 (FIG. 10). Also, a second latch member 396 that is analogous to first latch member 176 is visible. A pin or ball portion 400 of the second latch member 396 that is urged inward is visible. The pin or ball portion 400 is urged inward and that engages an indention (analogous to indention 380; see indention 402 in FIG. 11) of a second latch socket (not visible but on the catty-corner from the first latch socket 180 and substantially analogous to it). The second guide pin 392 may be longer than the first guide pin 168 and the second latch socket may be deeper so that the first compartment 124 and second compartment 128 cannot be mated in the wrong direction or orientation. The second latch member 396 also has a ledge or protrusion 404 that like ledge 384 mates with a ledge-receiving portion (see 406 in FIG. 11) of the second latch socket 403 (FIG. 11).

Figure 8:
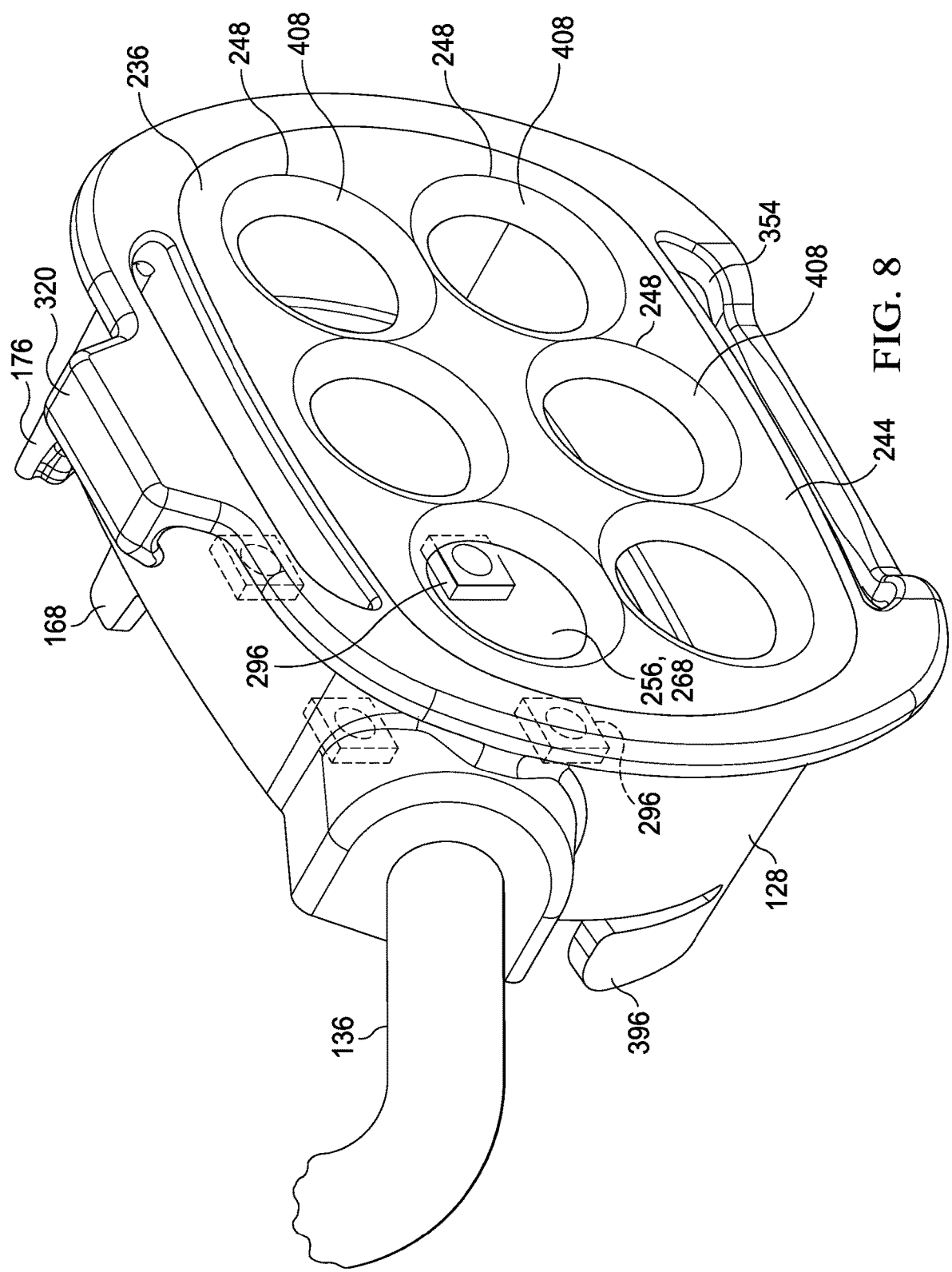
FIG. 8 is a schematic, perspective view from a bottom of the second compartment.

Referring now primarily to FIG. 8 is a schematic, perspective view from a bottom (or the orientation shown) of the second compartment 128 of the illustrative embodiment of the medical device 108. This view clearly shows the second floor member 236 and the one or more apertures 248 that are used to allow skin to be pulled into the second interior 280 of the second compartment 128. This view also shows how in some illustrative embodiments the one or more apertures 248 each have a rounded edge 408, which includes a smooth corner or beveled portion or staged portion or small radius portion, rather than a tight orthogonal corner. The rounded edge 408 is more comfortable for the patient 104 having his or her skin pulled into the apertures 248. In this illustrative embodiment, the one or more apertures 248 comprises six apertures with two parallel rows of three. It should be understood that other numbers may be used, such as 1, 2, 3, 4, 5, 7, 8, or more, and other patterns might be used. In one embodiment, the apertures 248 are each sized between 0.1 and 12 mm, and in one embodiment, six apertures of 10 mm each are used for a harvesting area of about 4.7 $cm^2$. In use, some of apertures 248 may be covered up with tape if fewer apertures are desired.

While not explicitly visible in FIG. 8, in one illustrative embodiment, the second side 264 of the second ceiling member 256, and in particular of the second printed circuit board 268, is covered with the heating element 292 (FIG. 3) that goes back and forth and covers the free area of the second printed circuit board 268. In this way, the heat applied in the second compartment 128 is evenly distributed over the area. The power to the heating element 292 can be regulated in terms of voltage to control the temperature or the power may be cycled with duration of the cycles being used to control the temperature. The control unit 112 and the electrical controller 144 may include an algorithm that cuts off the power or begins to cycle the power once the temperature rise in the second compartment is at some percentage less than 100 of the target temperature so that there is no overrun. The interior of the second chamber can heat quickly; for example, in one illustrative prototype, the heating time for the second compartment 128 from room temperature to target temperature was less than 30 seconds. This may provide for better heating and more accuracy. The temperature may be set by the user using the input controls 156 (FIG. 1) or turned off. In some embodiments, the default temperature is 40° C. and the adjustable range in one embodiment is between 30° C. and 80° C. In another embodiment, the adjustable range is between 37° C. and 50° C.

Figure 9:
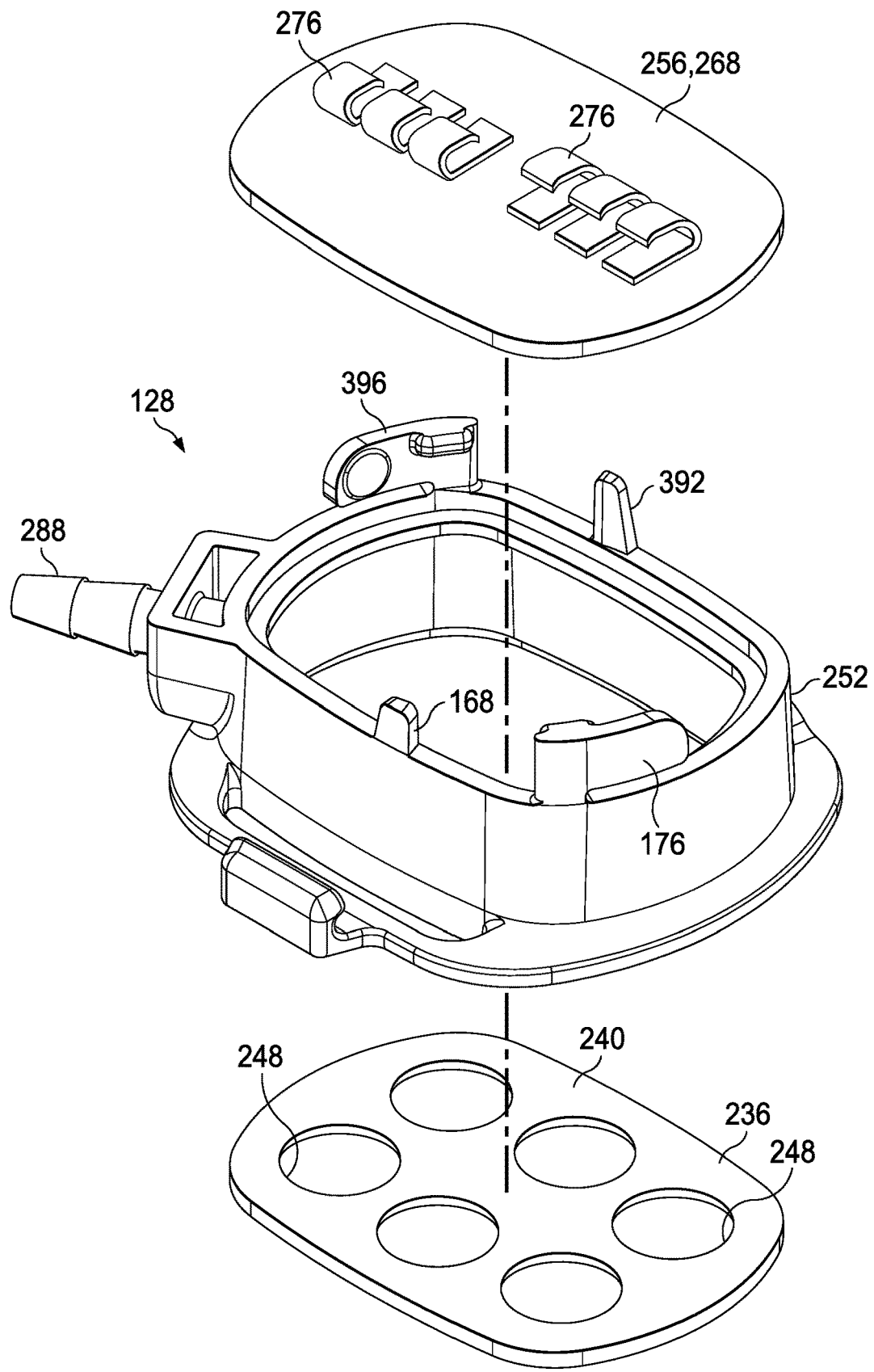
FIG. 9 is a schematic, exploded, perspective view of an illustrative embodiment of a second compartment of an illustrative embodiment of a medical device for harvesting epidermal tissue from a patient.

Referring now primarily to FIG. 9, a schematic, exploded, perspective view of an illustrative embodiment of the second compartment 128 of an illustrative embodiment of the medical device 108 for harvesting epidermal tissue from a patient 104 is presented. The second compartment 128 and first compartment 124 have been shown having a generally rectangular shape in plan view, but it should be understood that other shapes, circular, square, or others, may be used as well.

Referring now primarily to FIG. 10, a schematic, perspective view from a side of the first compartment 124 of an illustrative embodiment of the medical device 108 for harvesting epidermal tissue from a patient 104 is presented. In this view, one may see a second pin socket 412 and a second latching socket 416.

Referring now primarily to FIG. 11, a schematic, elevation view of the first compartment 124 of an illustrative embodiment of the medical device 108 for harvesting epidermal tissue from a patient 104 is presented. In this view, the conductor cable aperture 224 is clearly visible.

Referring now primarily to FIG. 12, a schematic, bottom plan view of the first compartment 124 of an illustrative embodiment of the medical device 108 for harvesting epidermal tissue from a patient 104 is presented. In this view, another illustrative embodiment of the first floor member 184 is clearly shown. The first floor member 184 comprises the first printed circuit board 188. The first printed circuit board 188 in this embodiment is shown with electrical contacts/pads 272 taking different shapes, e.g., circles and extended pads. Other shapes may be used including curled or spring loaded contacts as suggested by counterpart contacts 276 in FIG. 3.

In operation, the system 100 for harvesting epidermal tissue from a patient 104 is used by placing the control unit 112 near the patient, e.g., a meter (37 inches) away. The medical device 108 is prepared by releasably locking the first compartment 124 to a fresh disposable second compartment 128. The mated medical device 108 is placed with the second side of the second floor member against the patient at a desired location, e.g., a leg as shown in FIG. 1, an arm, hip, stomach, back, or elsewhere.

A securing strap is secured to one securing arm 320 and then run around the patient's 108 limb or torso and then looped through the securing arm aperture 354 on the other securing arm 352 and tightened into position. If not already done, the conductor cable 132 is connected to the control unit 112 and the first compartment 124 and the reduced-pressure conduit 136 is fluidly coupled between the second compartment 128 and the control unit 112. The desired temperature is set on the control unit 112 using the input controls 156 and treatment activated on the control unit 112. Optionally, the reduced-pressure may be adjusted by a negative pressure regulator on the control unit 112 controlled manually or with the electronics in the control unit 112. Upon powering up of the control unit 112, the LED lights 296 are activated, and upon treatment commencement, the heating element 292 is activated, the thermal sensor 300 is monitored, and a timer may also be activated.

As the reduced pressure is applied in the second interior portion 280 of the second compartment 128, the skin is pulled into the apertures 248 of the second floor member 236 and blisters form over time (see FIG. 13) as the epidermis is separated from the dermis. The clinician can view the blisters through the second plurality of side walls 252 that are transparent. When deemed ready, based mainly on color change or other visible characteristics of the blister, input controls 156 of the control unit 112 may be used to deactivate the medical device 108 and it can then be removed. The blisters are then harvested, or, in cases where the blister fluid is wanted, the fluid removed from the blister. The blister(s) may be "popped," held with tweezers and cut with a scalpel or other harvesting technique. In other embodiments, the blister(s) may be shaved or cut.

The second compartment 128 and the first compartment 124 are then separated. For example, the twist lock 164 shown in some embodiments above may be twisted to release them. Then the second compartment 128 and reduced-pressure conduit 136 may be thrown away.

During operation, the electronic controller 144 monitors data and can provide safety features. For example, the electronic controller 144 can shut down operation if the thermal sensor indicates a temperature higher than the normal operating range. Or, if a thermal sensor fails, the unit may turn off power to the heating element 292, turn off power to the fluid pump 140, or sound an alarm.

Figure 13:
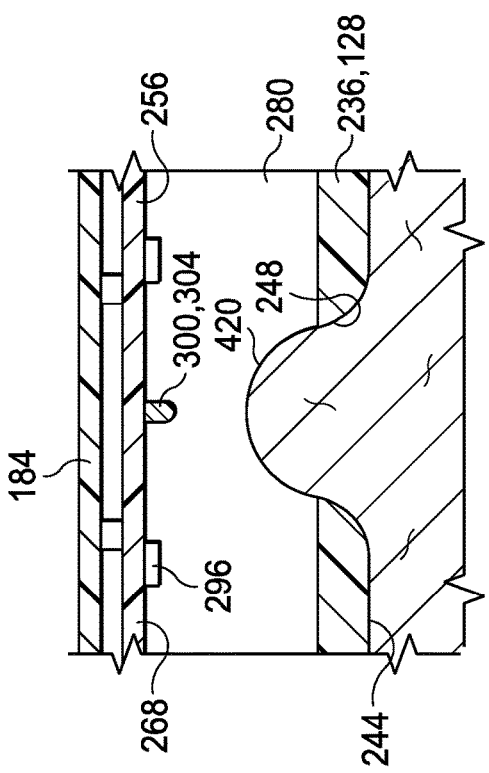
FIG. 13 is a schematic, elevational cross-section of a portion of a medical device for harvesting epidermal tissue from a patient showing skin being pulled through an aperture and into an interior of the second compartment.

Referring now primarily to FIG. 13, a schematic, elevational cross-section of a portion of a medical device 108 for harvesting epidermal tissue from a patient 104 is presented. This view shows skin 420 being pulled through an aperture 248 and into the interior 280 of the second compartment 128.

Referring now primarily to FIG. 14, a schematic, perspective view showing illustrative embodiments of two medical devices 108 for harvesting epidermal tissue from a patient 104 wherein the two medical devices 108 are coupled together. The two medical devices 108 are coupled together using the first securing arm 320 of one to connect—hook—the securing arm aperture 332 of the second securing arm that is adjacent on the other medical device.

Many variations and alternatives may be used. In one alternative embodiment, a mirror is added to a portion of an interior of the second plurality of side walls 252 to facilitate viewing of the blisters; the mirror may be angled down.

In one alternative embodiment, the first compartment contains all of the electronics. The first compartment has the thermistor and heating element in it. The second compartment mates with the first compartment with a gasket on the ledge and forms a single chamber. Electrical cabling goes into the first portion and the suction or reduced pressure line goes into the second portion but again, there is only one chamber in this embodiment.

The various illustrative embodiments present many possible advantages and benefits. In some, the second compartment is included and is disposable, and thus requires no cleaning; the first compartment is protected from contamination; a thermal sensor is directly inside the second compartment, which may provide for more accurate temperature control; LED lights inside the second compartment provide excellent lighting of the blisters that are forming; the clear plastic side walls of the second plurality of sidewalls allows the skin and blister formation to be readily visible; that the medical device is secured to the patient using securing arms at the very bottom of the device along with a hook-and-loop fastening strap or other strap results in there being no strap up on the device to impair the view into the second compartment through the transparent side walls; the power supplied to the heating element on the second side of the second ceiling allows for temperature control over the range and not necessarily limited to discrete settings and is also distributed over the surface.

Although the present invention and its advantages have been disclosed in the context of certain illustrative, non-limiting embodiments, it should be understood that various changes, substitutions, permutations, and alterations can be made without departing from the scope of the invention as defined by the claims. It will be appreciated that any feature that is described in a connection to any one embodiment may also be applicable to any other embodiment.

What is claimed:

1. A medical device for harvesting epidermal tissue from a patient, the medical device comprising:
   a first compartment comprising:

a first floor member comprising a first printed circuit board and having a first side and a second side, wherein the second side is outward facing when in an unmated position, a first plurality of side walls coupled to the first floor member, a first ceiling member coupled to the first plurality of side walls, wherein the first floor member, the first plurality of side walls, and the first ceiling member form the first compartment having a first interior portion and a first exterior shell, a plurality of conductive wires coupled to the first printed circuit board; and a second compartment comprising:

a second floor member having a first side and a second side, wherein the the second side of the second floor member is outward facing, and wherein the second floor member is formed with one or more apertures for receiving a portion of the patient's skin, a second plurality of side walls coupled to the second floor member, a second ceiling member coupled to the second plurality of side walls, wherein the second ceiling member has a first side and a second side, wherein the first side of the second ceiling member is outward facing when in an unmated position, wherein the second ceiling member comprises a second printed circuit board that is electrically coupled with the first printed circuit board when in a mated position, wherein the second floor member, the second plurality of side walls, and the second ceiling member form the second compartment having a second interior portion and a second exterior shell, wherein the second compartment forms a substantially fluid-tight compartment except for the one or more apertures for receiving the patient's skin and a reduced-pressure port;

a reduced-pressure conduit fluidly coupled to the reduced-pressure port and thereby to the second interior portion; and wherein, in the mated position, the first compartment is releasably coupled to the second compartment with the second side of the first floor member facing the first side of the second ceiling member.

2. The medical device for harvesting epidermal tissue from a patient of claim 1, wherein, the second side of the first floor member comprises a first plurality of electrical contacts/pads and wherein the first side of the second ceiling member comprises a second plurality of electrical contacts/pads, and wherein, in the mated position, the first plurality of electrical contacts/pads are electrically coupled to the second plurality of electrical contacts/pads.

3. The medical device for harvesting epidermal tissue from a patient of claim 1, wherein the one or more apertures for receiving a portion of the patient's skin formed in the second floor member comprises one or more rounded apertures, each having at least a rounded corner at an entrance from the second side of the second floor member.

4. The medical device for harvesting epidermal tissue from a patient of claim 1, wherein the second side of the second ceiling member comprises a heating element that extends over a majority of the surface of the second side of the second ceiling member on the second printed circuit board.

5. The medical device for harvesting epidermal tissue from a patient medical device for harvesting epidermal tissue from a patient of claim 1, further comprising at least one LED positioned within the second compartment.

6. The medical device for harvesting epidermal tissue from a patient of claim 1, further comprising at least one thermal sensor electrically coupled to the second printed circuit board and positioned within the second compartment.

7. The medical device for harvesting epidermal tissue from a patient of claim 1, wherein the first compartment further comprises a first portion of a twist lock, and wherein the second compartment further comprises a second portion of the twist lock that is sized and configured to mate with the first portion of the twist lock to form a releasable coupling when in the mated position.

8. The medical device for harvesting epidermal tissue from a patient of claim 1, wherein the first compartment is formed with an aperture for receiving a plurality of electrical wires into the first interior portion.

9. The medical device for harvesting epidermal tissue from a patient of claim 1, wherein the second plurality of side walls are formed from a transparent material.

10. The medical device for harvesting epidermal tissue from a patient of claim 1, wherein the second plurality of side walls has a first portion proximate the second ceiling member and a second portion proximate the second floor member, and further comprising a first securing arm extending from an exterior side of the second plurality of side walls proximate the second portion of the second plurality of side walls and a second securing arm extending from the exterior side of the second plurality of side walls proximate the second portion of the second plurality of side walls opposite the first securing arm.

11. The medical device for harvesting epidermal tissue from a patient of claim 1, further comprising:

wherein the second plurality of side walls has a first portion proximate the second ceiling member and a second portion proximate the second floor member, a first securing arm extending from an exterior side of the second plurality of side walls proximate the second portion of the second plurality of side walls;

a second securing arm extending from the exterior side of the second plurality of side walls proximate the second portion of the second plurality of side walls and opposite the first securing arm;

wherein the first securing arm is formed with a first strap aperture for receiving a securing strap; and wherein the second securing arm is formed with a second strap aperture for receiving the securing strap.

12. The medical device for harvesting epidermal tissue from a patient of claim 11, wherein the first securing arm is further formed with an extension portion coupled to the second plurality of side walls and extending substantially perpendicular to the second plurality of side walls and having a gripping portion at a distal end of the extension portion that is angled away from the second floor member, wherein the gripping portion has a hook-shaped end and is sized and configured to mate with a strap aperture of another medical device.

13. The medical device for harvesting epidermal tissue from a patient of claim 1, wherein the second compartment is disposable.

14. The medical device for harvesting epidermal tissue from a patient of claim 1, further comprising:

wherein the second plurality of side walls has a first portion proximate the second ceiling member and a second portion proximate the second floor member, a first securing arm extending from an exterior side of the second plurality of side walls proximate the second portion of the second plurality of side walls;
a second securing arm extending from the exterior side of the second plurality of side walls proximate the second portion of the second plurality of side walls and opposite the first securing arm;
wherein the first securing arm is formed with a first strap aperture for receiving a securing strap;
wherein the second securing arm is formed with a second strap aperture for receiving the securing strap; and
wherein the first securing arm or the second securing arm is formed with a coupling hook sized and configured to mate with a first strap aperture or a second strap aperture of another analogous medical device for harvesting epidermal tissue from a patient.

15. The medical device for harvesting epidermal tissue from a patient of claim 1, further comprising:
wherein the second side of the first floor member comprises a first plurality of electrical contacts/pads and wherein the first side of the second ceiling member comprises second plurality of electrical contacts/pads, and wherein, in the mated position, the first plurality of electrical contacts/pads is electrically coupled to the second plurality of electrical contacts/pads;
wherein the second ceiling member comprises a heating element that extends over a majority of a side of the surface of the second ceiling member on the second printed circuit board;
at least one LED positioned within the second compartment; and
at least one thermal sensor electrically coupled to the second printed circuit board and positioned within the second compartment.

16. The medical device for harvesting epidermal tissue from a patient of claim 1, further comprising:
wherein the second side of the first floor member comprises a first plurality of electrical contacts/pads and wherein the first side of the second ceiling member comprises a second plurality of electrical contacts/pads, and wherein, in the mated position, the first plurality of electrical contacts/pads is electrically coupled to the second plurality of electrical contacts/pads;
wherein the second side of the second ceiling member comprises a heating element that extends over a majority of the surface of the second side of the second ceiling member on the second printed circuit board;
at least one LED positioned within the second compartment;
at least one thermal sensor electrically coupled to the second printed circuit board and positioned within the second compartment;
wherein the first compartment further comprises a first portion of the twist lock, and wherein the second compartment further comprises a second portion of a twist lock that is sized and configured to mate with the first portion of the twist lock to form a releasable coupling when in the mated position;
wherein the first compartment is formed with an aperture for receiving a plurality of electrical wires into the first interior portion;
wherein the second plurality of side walls are formed from a transparent material;
wherein the second plurality of side walls has a first portion proximate the second ceiling member and a second portion proximate the second floor member,
a first securing arm extending from an exterior side of the second plurality of side walls proximate the second portion of the second plurality of side walls;
a second securing arm extending from the exterior side of the second plurality of side walls proximate the second portion of the second plurality of side walls and opposite the first securing arm;
wherein the first securing arm is formed with a first strap aperture for receiving a securing strap; and
wherein the second securing arm is formed with a second strap aperture for receiving the securing strap.

17. A system for harvesting epidermal tissue from a patient, the system comprising:
a control unit comprising:
a housing,
a reduced-pressure pump within the housing, and
an electrical controller;
a harvesting medical device comprising:
a first compartment comprising:
a first floor member comprising a first printed circuit board and having a first side and a second side, wherein the second side is outward facing when in an unmated position,
a first plurality of side walls coupled to the first floor member,
a first ceiling member coupled to the first plurality of side walls,
wherein the first floor member, the first plurality of side walls, and the first ceiling member form the first compartment having a first interior portion and a first exterior shell,
a plurality of conductive wires coupled to the first printed circuit board;
a second compartment comprising:
a second floor member having a first side and a second side, wherein the the second side of the second floor member is outward facing, and wherein the second floor member is formed with one or more apertures for receiving a portion of the patient's skin,
a second plurality of side walls coupled to the second floor member,
a second ceiling member coupled to the second plurality of side walls, wherein the second ceiling member has a first side and a second side, wherein the first side of the second ceiling member is outward facing when in an unmated position, wherein the second ceiling member comprises a second printed circuit board that is electrically coupled with the first printed circuit board when in a mated position,
wherein the second floor member, the second plurality of side walls, and the second ceiling member form the second compartment having a second interior portion and a second exterior shell, wherein the second compartment forms a substantially fluid-tight compartment except for the one or more apertures for receiving the patient's skin and a reduced-pressure port;
a reduced-pressure conduit fluidly coupled to the reduced-pressure port and to the reduced-pressure pump in the control unit;
a conductor cable electrically coupling the first printed circuit board and the electrical controller in the control unit; and
wherein, in the mated position, the first compartment is releasably coupled to the second compartment with the second side of the first floor member facing the first side of the second ceiling member.

18. The system for harvesting epidermal tissue from a patient of claim 17, wherein, the second side of the first floor member comprises a first plurality of electrical contacts/pads and wherein the first side of the second ceiling member comprises a second plurality of electrical contacts/pads, and wherein, in the mated position, the first plurality of electrical contacts/pads is electrically coupled to the second plurality of electrical contacts/pads.

19. The system for harvesting epidermal tissue from a patient of claim 17, wherein the one or more apertures for receiving a portion of the patient's skin formed in the second floor member comprises a plurality of rounded apertures each having at least a rounded corner at an entrance from the second side of the second floor member.

20. The system for harvesting epidermal tissue from a patient of claim 17, wherein the second side of the second ceiling member comprises a heating element that extends over a majority of the surface of the second side of the second ceiling member on the second printed circuit board.

21. The system for harvesting epidermal tissue from a patient of claim 17, further comprising at least one LED positioned within the second compartment.

22. A method of harvesting epidermal tissue from a patient, the method comprising:
providing a medical device that comprises:
a first compartment comprising:
a first floor member comprising a first printed circuit board and having a first side and a second side, wherein the second side is outward facing when in an unmated position,
a first plurality of side walls coupled to the first floor member,
a first ceiling member coupled to the first plurality of side walls,
wherein the first floor member, the first plurality of side walls, and the first ceiling member form the first compartment having a first interior portion and a first exterior shell,
a plurality of conductive wires coupled to the first printed circuit board;
a second compartment comprising:
a second floor member having a first side and a second side, wherein the the second side of the second floor member is outward facing, and wherein the second floor member is formed with one or more apertures for receiving a portion of the patient's skin,
a second plurality of side walls coupled to the second floor member,
a second ceiling member coupled to the second plurality of side walls, wherein the second ceiling member has a first side and a second side, wherein the first side of the second ceiling member is outward facing when in an unmated position, wherein the second ceiling member comprises a second printed circuit board that is electrically coupled with the first printed circuit board when in a mated position, and
wherein the second floor member, the second plurality of side walls, and the second ceiling member form the second compartment having a second interior portion and a second exterior shell, wherein the second compartment forms a substantially fluid-tight compartment except for the one or more apertures for receiving the patient's skin and a reduced-pressure port;
a reduced-pressure conduit fluidly coupled to the second interior portion; and
wherein, in the mated position, the first compartment is releasably coupled to the second compartment with the second side of the first floor member facing the first side of the second ceiling member;
applying reduced pressure to the second interior portion of the second compartment to pull the patient's skin into the one or more apertures through the second floor member;
applying electrical power to a heating element on the second printed circuit board; and
removing epidermal tissue once a plurality of blisters is formed that extend through the one or more apertures through the second floor member.

\* \* \* \* \*